(12) United States Patent
Greenwood et al.

(10) Patent No.: US 7,884,222 B2
(45) Date of Patent: Feb. 8, 2011

(54) PROCESS FOR THE PRODUCTION OF TIBOLONE

(75) Inventors: Alan K. Greenwood, Hertfordshire (GB); Derek McHattie, Hertfordshire (GB); Parveen Bhatarah, Hertfordshire (GB)

(73) Assignee: Resolution Chemicals Limited, Hertfordshire (GB)

( * ) Notice: Subject to any disclaimer, the term of this patent is extended or adjusted under 35 U.S.C. 154(b) by 1115 days.

(21) Appl. No.: 10/548,114

(22) PCT Filed: Mar. 3, 2004

(86) PCT No.: PCT/GB2004/000887

§ 371 (c)(1),
(2), (4) Date: Dec. 23, 2005

(87) PCT Pub. No.: WO2004/078774

PCT Pub. Date: Sep. 16, 2004

(65) Prior Publication Data

US 2006/0173201 A1    Aug. 3, 2006

(30) Foreign Application Priority Data

Mar. 4, 2003    (GB) ................. 0304927.7

(51) Int. Cl.
C07J 7/00    (2006.01)
A61K 31/56    (2006.01)

(52) U.S. Cl. ...................... 552/597; 514/178
(58) Field of Classification Search ............... 514/178; 552/597
See application file for complete search history.

(56) References Cited

U.S. PATENT DOCUMENTS

| | | | |
|---|---|---|---|
| 2,798,879 A | | 9/1957 | Donia et al. |
| 2,957,933 A | * | 10/1960 | Pommer et al. ............. 554/154 |
| 3,340,279 A | | 9/1967 | de Jongh et al. ......... 260/397.4 |
| 3,475,465 A | | 10/1969 | de Winter et al. ........ 260/397.4 |
| 3,515,719 A | | 6/1970 | Campbell et al. |
| 3,642,839 A | * | 2/1972 | Furst et al. .................. 552/632 |
| 3,655,649 A | * | 4/1972 | Habermehl et al. .......... 540/84 |
| 4,083,973 A | * | 4/1978 | van der Vies ............... 514/178 |
| 4,311,646 A | | 1/1982 | Nitta et al. ............... 260/397.4 |
| 6,313,108 B1 | * | 11/2001 | Loozen et al. ............. 514/178 |
| 2005/0090476 A1 | * | 4/2005 | Van Buggenum et al. ... 514/177 |

FOREIGN PATENT DOCUMENTS

| | | |
|---|---|---|
| DE | 43 08 095 A1 | 9/1994 |
| EP | 0 555 845 A3 | 8/1993 |
| EP | 0 389 035 B1 | 12/1993 |
| EP | 1 275 379 A2 | 1/2003 |
| EP | 1 121 375 B1 | 5/2003 |
| FR | 2 311 030 | 1/1977 |
| GB | 1 527 161 | 10/1978 |
| WO | WO 90/08128 | 7/1990 |
| WO | WO 93/10141 | 5/1993 |
| WO | WO 98/32718 | 7/1998 |
| WO | WO 99/67270 | 12/1999 |
| WO | WO 99/67271 | 12/1999 |
| WO | WO 00/23460 | 4/2000 |
| WO | WO 00/56757 | 9/2000 |
| WO | WO 00/59920 | 10/2000 |
| WO | WO 00/66611 | 11/2000 |
| WO | WO 00/66613 | 11/2000 |
| WO | WO 01/27132 A1 | 4/2001 |

OTHER PUBLICATIONS

Campbell et al. J. Am. Chem. Soc. 81(15), 4069-4074, 1959.*
Takeda et al. J. Org. Chem. 51, 4731-33, 1986.*
FDA drug details: nandrolone. Approved Jan. 13, 1984.*
CAS registry records (STN).*
"7-Methylestrenes", Chemical Abstracts, vol. 64, 1966, col. 12759.
Bascoul et al., "Synthese Et Caracteres Analytiques De Quelques Esters D'Enol De La Testosterone Et D'Acides Gras." Eur. J. Steroids 1967, 2—pp. 557-567.
Groen et al., "Biomemetic total synthesis of steroids II: Stereoselective synthesis of 7α-methyl-19-norsteroids" Recueil, Journal of the Royal Netherlands Chemical Society 97/11, Nov. 1978 pp. 301-304.
Kolvoda et al., "Helvetica Chimica ACTA 50" Volumen 50, Fasciculus 1 (1967) No. 32-33: (English summary on last page).
Shapiro et al., "A Concomitant Ethinylation and Esterification Reaction" The Journal of Organic Chemistry vol. 33, No. 4, Apr. 1968 pp. 1673-1675.
Wieland et al., "Helvetica Chimica ACTA 50" Volumen 50, Fasciculus 1 (1967) No. 34 (English summary on last page).
van Vliet et al., "An alternative synthesis of 17β-hydroxy-7α-methyl-19-nor-17 α-pregn-5(10)-en-20-yn-3-one (Org OD14)" Recueil de Travaux Chimiques des Pays-Bas. 105/4 Apr. 1986 pp. 111-115.

(Continued)

Primary Examiner—Frederick Krass
Assistant Examiner—Adam Milligan
(74) Attorney, Agent, or Firm—Marshall, Gerstein & Borun LLP

(57) ABSTRACT

A process for the syntheses of 17β-hydroxy-7α-methyl-19-nor-17α-pregn-5(10)-ene-20-yne-3-one (tibolone, 11) and intermediates useful for the synthesis thereof.

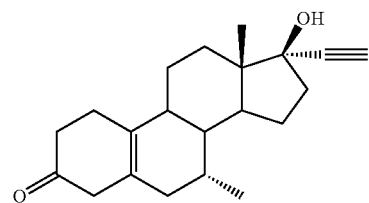

(11)

19 Claims, No Drawings

OTHER PUBLICATIONS

Vesely et al., "Steroid Derivativesl LIX", "Kinetics of Alkali Hydrolysis of Some Testosterone Esters in 70% Dioxane", Collection Czechoslov. Chem. Commun./ vol. 34 1969 pp. 685-689.
Document XP009023609; Joyce F. Grunwell et al., "Antiprogestational Agents. The Synthesis of 7-Alkyl Steroidal Ketones With Anti-Implantational And Antidecidual Activity," *Steroids*, vol. 27, No. 6; p. 759-771, Jun. 1976.
Document XP-002118688; Mitchell A. Avery et al., "Synthesis and Testing of 17aβ-hydroxy-7α-methyl-D-homoestra-4,16-dien-3-one: a highly potent orally active androgen," *Steroids*, vol. 55, p. 59-64 Feb. 1990.
Document XP-002204811; Campbell et al., "7α-methyl-18-norsteroids: A new class of potent anabolic and androgenic hormones," *Steroids*, vol. 1, p. 317-324.
Written Opinion of The International Searching Authority for counterpart International Application No. PCT/GB2004/000887.
International Search Report for counterpart International Application No. PCT/GB2004/000887; Date of Mailing Jun. 4, 2004.

* cited by examiner

PROCESS FOR THE PRODUCTION OF TIBOLONE

The present invention is directed to the synthesis of 17β-hydroxy-7α-methyl-19-nor-17α-pregn-5(10)-ene-20-yne-3-one (tibolone), and intermediates useful for the synthesis of tibolone and purification thereof. Tibolone has the following structural formula:

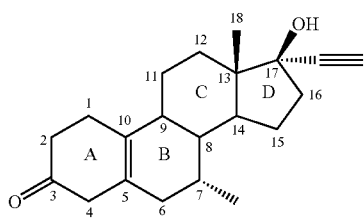

Tibolone is a synthetic 19-norandrosterone having weak oestrogenic, androgenic and progestogenic activity, and is useful for the treatment of menopausal syndrome.

Procedures for the synthesis of tibolone have been disclosed in the art. For example, U.S. Pat. No. 3,340,279, discloses a procedure starting from 7α-methyl-oestradiol-3-methylether:

U.S. Pat. No. 3,340,279 does not disclose how the starting material, 7α-methyl-oestradiol-3-methylether, should be obtained. In this prior art procedure, 7α-methyloestradiol-3-methyl ether is reduced by a Birch reduction process using lithium in liquid ammonia to produce the 3-methoxyoestra-2,5(10)diene. The 17-hydroxy group of the product is oxidised to produce the corresponding ketone. Reaction of this ketone with potassium acetylide, followed by hydrolysis with aqueous oxalic acid in methanol produces the product tibolone.

The above procedure suffers from several drawbacks. According to the disclosed process, two chromatographic procedures are required. In particular, the product isolated from the oxidation step requires purification by chromatography over silica gel. A second chromatography step is required in order to purify the product tibolone. The need for chromatographic purification procedures is undesirable in a large-scale operation because only relatively small amounts of product can be purified at a time and large quantities of waste, in the form of solvents and silica, are generated. This means that considerations with regards to safe disposal are necessary.

A further disadvantage with the above procedure is that the ethynylation reaction requires the use of potassium acetylide, which is formed from potassium metal and acetylene. Potassium metal is highly reactive and potassium acetylide is extremely corrosive. Therefore, the use of these reagents in large-scale operations is undesirable.

Van Vliet et al., in Recl. Trav. Chim. Pays-Bas, 105, 111-115 (1986), discloses a procedure for the synthesis of tibolone, starting from 17β,19-dihydroxy-androsta-4,6-dien-3-one 17,19-diacetate:

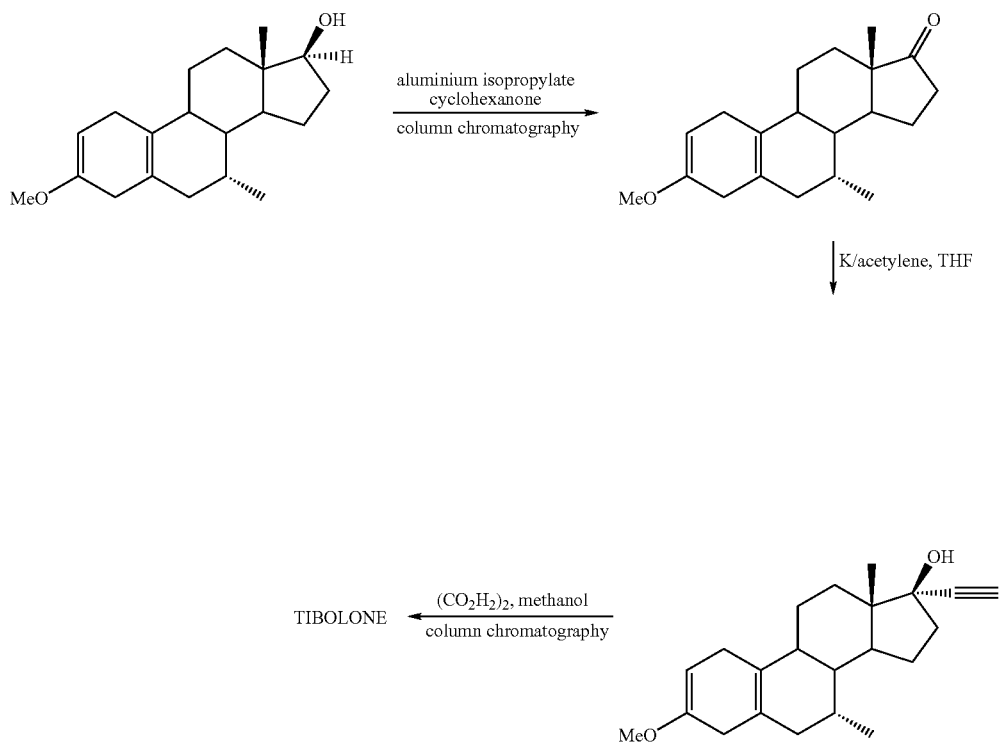

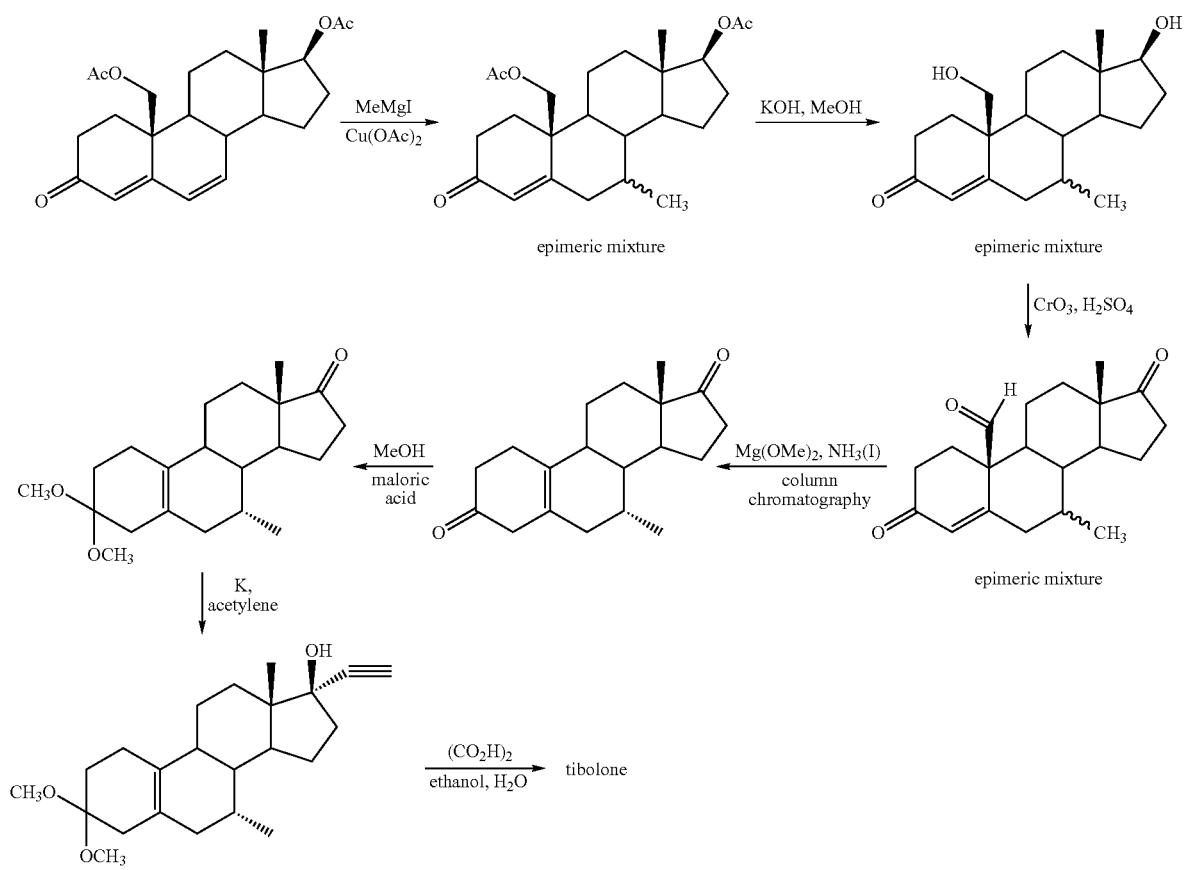

Thus, in the above procedure, the starting material, which is prepared from 3β-hydroxyandrost-5-en-17-one-3-acetate in a multi-step procedure, is subjected to a copper-catalysed conjugate addition reaction with methyl-magnesium iodide at −40° C. to form an epimeric mixture of 7α- and 7β-methylandrost-4-en-3-ones.

The resulting epimeric mixture is subjected to saponification to produce the corresponding epimeric mixture of alcohols in a 7α:7β ratio of about 4:1. It is stated that the epimeric mixtures of both the ester and alcohols are difficult to separate by chromatography and that attempts to isolate the 7α-isomer of the alcohol by repeated crystallisation resulted in poor yields.

In the next step, the epimeric mixture of alcohols is oxidised with chromic acid to produce an epimeric mixture of the corresponding aldehydes. It is disclosed that although the desired 7α-isomer of the aldehyde can be isolated from the reaction mixture, yields of only about 30% are achieved. The 7β-isomer of the aldehyde, on the other hand, could not be separated from the 7α-isomer, and produced only a mixture of 7':7β in a 4:1 ratio. The separated 7α-aldehyde is then subjected to a reduction reaction by treatment with magnesium methoxide in liquid ammonia, to form the dione. Treatment of the dione with methanol and malonic acid forms the 3,3-dimethylacetal compound. Ethynylation of the 17-carbon, followed by removal of the protecting group using aqueous oxalic acid produces tibolone.

It can be seen from the above discussion that this procedure also suffers from severe drawbacks that make it unsuitable for large-scale production of tibolone. A major problem in the van Viet et al. procedure is attributable to the methylation step, which produces a mixture of the 7α and 7β epimers in a ratio of about 4:1. In addition to the fact that these epimers are extremely difficult to separate, the unwanted 7β epimer is present in significant quantities in two of the subsequent reaction steps. This means that when this process is employed in the synthesis of tibolone, which has the 7α-configuration, reagents are unnecessarily wasted in converting the unwanted 7β-epimer.

Further, although it is reported that the 7α-aldehyde is separable from its 7β epimer, this separation appears to be achievable only at the expense of a loss of a significant portion of the desired 7α-aldehyde, with only 30% yield being reported. Furthermore, the separation requires a column chromatography procedure.

A further disadvantage with this procedure is that the oxidation step requires the use of chromium trioxide. The use of chromium salts in a large-scale manufacturing process is undesirable, since the safe disposal of chromium-containing waste must be considered. This may add to the cost of the overall operation.

It is thus apparent that the van Vliet process discussed above is unsuitable for the large-scale production of tibolone.

In view of the prior art, it would be desirable to provide a superior process for the production of intermediates useful for the production of tibolone, as well as a procedure for the production of tibolone. Further, it is desirable that the process employs readily available starting materials. It is also desirable that the process enables easy isolation of the intermediates and product tibolone and reduces the need for complex purification procedures. In particular, it is preferred that the process avoids, where possible, the need for purification of the intermediates and tibolone product by column chromatography. It is also desirable that the process can be scaled up to enable the large-scale production (e.g. in tens of kilogram quantities) of tibolone.

According to one aspect of the present invention, there is provided a process for the production of a compound of formula (6):

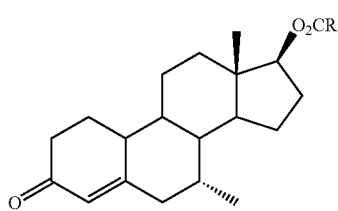

(6)

wherein R represents $C_1$ to $C_{20}$ alkyl, $C_6$ to $C_{10}$ aryl, $C_7$ to $C_{20}$ aralkyl, $C_3$ to $C_8$ cycloalkyl and $C_7$ to $C_{20}$ cycloalkyl, the process comprising the steps of:

(i) methylating the carbon atom at the 7-position of a compound of formula (5):

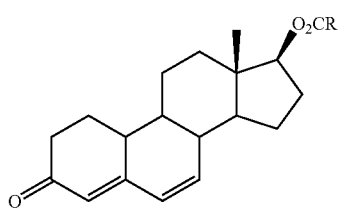

(5)

to form a compound of formula (5a):

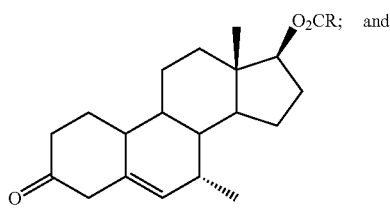

(5a)

(ii) isomerising the C=C double bond of the compound of formula (5a).

Preferably, R represents $C_1$ to $C_{10}$ alkyl. Even more preferably, R represents $C_1$ to $C_6$ alkyl (especially methyl).

The compound of formula (6) is a key intermediate in the production of tibolone. The methylation reaction involves a conjugate addition of the alkyl Grignard methylating reagent at the 7-carbon. A preferred methylating agent for this process is a methyl-magnesium halide, especially methyl-magnesium chloride. Methyl-magnesium halides are readily available as solutions (e.g. 10-30% solutions) in various solvents such as tetrahydrofuran (THF) and diethylether. In particular, methyl-magnesium chloride is readily available as a solution in tetrahydrofuran.

Typically, the methylating agent is added in an amount of 1.2 to 1.8 equivalents with respect to the compound (5) starting material. Especially preferred amounts of methylating agent are within the range of 1.5 to 1.7 equivalents. Good results have been obtained when about 1.5 equivalents of the methyl-magnesium halide (especially chloride) is employed.

The methylation reaction is conducted in the presence of a copper(II) salt as catalyst. Examples of suitable copper(II) salts include copper(II) halides [such as copper(II) chloride], and copper(II) acetate. Copper(II) acetate is particularly preferred.

Amounts of the copper(II) catalyst can vary from 0.05 to 0.5 equivalents, preferably 0.1 to 0.3 equivalents, even more preferably 0.15 to 0.25 equivalents, with respect to the compound (5) starting material.

According to the invention, the methylation reaction is preferably carried out in the presence of an aprotic solvent. Suitable solvents include tetrahydrofuran, diethylether, dichloromethane and dimethylformamide. Tetrahydrofuran is an especially preferred solvent.

The methylation reaction is preferably carried out at low temperature. This has the advantage of minimising attack at the 7β-position. A further advantage of conducting the reaction at low temperature is that this may minimise side products formed by attack at other functional groups in the starting material, especially a possible competing 1,4 and 1,2 attack on the dienone system.

It is preferred that the methylation reaction is conducted at a temperature of less than 0° C., and more preferably at a temperature range of −80° C. to 0° C., and even more preferably at a temperature range of −60° C. to −15° C. Particularly good results have been obtained at temperature ranges of from −50° C. to −30° C., and especially at a temperature range of −45° C. to −35° C.

Typical reaction times for methylation process range from 1.5 hours up to 7 hours. It has been found that good results can be achieved with reaction times of from 3 to 5 hours. However, the reaction can be continued until near-complete conversion of the starting material is achieved [e.g. until less than 0.8%, preferably less than 0.5%, even more preferably 0.1% or less, of the starting material (5) remains].

The compound of formula (5a) can be isolated prior to the isomerisation step (ii). However, it is convenient to conduct steps (i) and (ii) in one pot, by which it is meant that the compound of formula (5a) is not isolated and purified before carrying out isomerisation step (ii).

This can be achieved by adding an aqueous mineral acid (e.g. hydrochloric acid) directly to the reaction mixture. It is preferred that the isomerisation step (ii) is conducted at a temperature range of below 20° C., preferably below 15° C., and even more preferably below 10° C. Good results can be achieved at temperature range of between 0° C. to 10° C.

The resulting product compound (6) may then be extracted from the reaction mixture using an organic solvent, particularly alkane solvents, such as hexanes or heptane.

Conveniently, the product (6) can be purified simply by crystallisation from a mixture of heptane and tert-butyl methyl ether, thus avoiding the need for chromatographic procedures. Alternatively, the solution can be used directly in the next stage without purification.

It has been unexpectedly found that by using the present methylation procedure, a 7α/7β, epimer selectivity ratio as high as 98:2 may be achieved. This is a significant improvement upon the procedure disclosed in Van Vliet et al. in Recl. Trav. Chim. Pays-Bas, 105, 111-115 (1986), in which a 7α/7β, selectivity ratio of only 4:1 is obtained in the reaction of the 10-$CH_2OAc$ derivative of compound (5). In addition, the present process is advantageous due to the high selectivity for the desired 1,6 attack versus the undesired 1,2 attack. In some cases, greater than 95% selectivity for 1,6 attack has been observed.

As well as the high 7α/7β selectivity ratio obtainable by the present procedure, it will be noted that the procedure according to the present invention is particularly advantageous because it avoids the need for chromatographic separation of the undesired 7β isomer from the desired 7α product. In view of the avoidance of any chromatographic purification procedure, and the high 7α/7β selectivity, high yields of the compound of formula (6) can be achieved. It has been found that yields of between 70-80% or greater can be achieved when carrying out the process of the present invention. The process is therefore amenable to large-scale commercial manufacturing operations.

The compound of formula (5a):

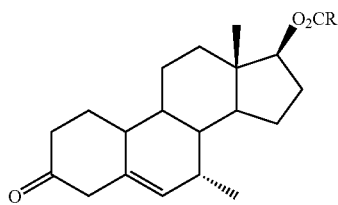

(5a)

wherein R represents $C_1$ to $C_{20}$ alkyl, $C_6$ to $C_{10}$ aryl, $C_7$ to $C_{20}$ aralkyl, $C_3$ to $C_8$ cycloalkyl and $C_7$ to $C_{20}$ alkaryl is novel and represents a further embodiment of the present invention.

Preferably, in the compound of formula (5a), R represents $C_1$ to $C_6$ alkyl or $C_6$ to $C_{10}$ aryl, with $C_1$ to $C_3$ alkyl (especially methyl) being especially preferred.

The starting material for the above process, compound (5), may be conveniently prepared from 9-nortestosterone (nandrolone) in a process comprising:

(i) protecting the 3-keto and 17-hydroxy group of nandrolone (I):

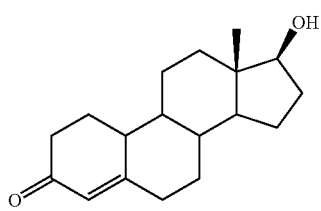

(1)

to produce a compound of formula (3):

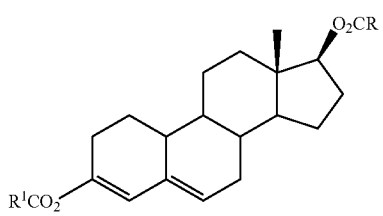

(3)

wherein R and $R^1$ may be the same or different and each represents $C_1$ to $C_{20}$ alkyl, $C_6$ to $C_{10}$ aryl, $C_3$ to $C_8$ cycloalkyl, $C_7$ to $C_{20}$ aralkyl or $C_7$ to $C_{20}$ alkaryl;

(ii) halogenating the carbon atom at the 6-position of the compound of formula (3) with a halogenating agent to form a compound of formula (4):

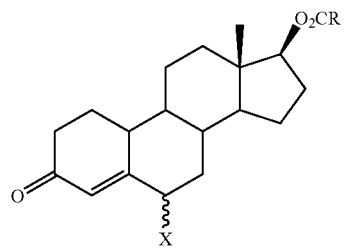

(4)

wherein X represents F, Cl, Br or I; and (iii) dehydrohalogenating the compound of formula (4).

Nandrolone is a commercially available steroid having anabolic activity.

Nandrolone may be converted to the compound of formula (3) by a procedure comprising:

(a) reacting nandrolone (1) with a compound $(RCO)_2O$ to produce a compound of Formula (2)

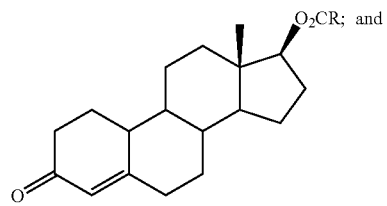

(2)

(b) reacting the compound of Formula (2) with $R^1$—CO—X wherein X is Cl, Br or I to produce the compound of Formula (3).

Alternatively, steps (a) and (b) can be reversed, i.e. nandrolone firstly with $R^1$—CO—X and subsequently contacting the so-formed product with $(RCO)_2O$. In a preferred procedure, nandrolone is contacted with a mixture containing $R^1$—CO—X and $(RCO)_2O$.

In the second, preferred method, nandrolone (1) can be converted to the diester compound of formula (3) by reaction with a compound of formula:

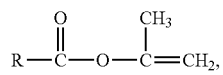

in the presence of an acid catalyst, for example, para-toluenesulfonic acid. The group R in the above formula can represent $C_1$ to $C_{20}$ alkyl, $C_6$ to $C_{10}$ aryl, $C_7$ to $C_{20}$ aralkyl, $C_3$ to $C_8$ cycloalkyl or $C_7$ to $C_{20}$ alkaryl. Preferably, R represents $C_1$ to $C_6$ alkyl, especially methyl. In a particularly preferred procedure, isopropenyl acetate, which is commercially available, is employed as the acetylating agent.

The esterification agent is usually employed in excess, typically in an amount of between 2.5 to 4 equivalents with respect to the nandrolone starting material. Preferably, 2.8 to 3.5 equivalents of the esterification agent are employed.

The para-toluene sulfonic acid is employed in catalytic quantities. Typically, amounts in the range of 0.01 to 0.1 equivalents may be used, with 0.03 to 0.07 being especially preferred.

The reaction is typically conducted at reflux temperature. The reaction is preferably conducted in a suitable solvent such as an alkyl acetate, wherein the alkyl group can be $C_1$ to $C_{20}$ straight chain or branched, with $C_1$ to $C_6$ alkyl preferred. In a particularly preferred procedure, isopropyl acetate is employed. Thus, according to a preferred procedure, nandrolone (1), para-toluene sulfonic acid and solvent (e.g. isopropyl acetate) are combined. The mixture may be heated to reflux temperature, whereupon the esterification agent (e.g. isopropenyl acetate) is added dropwise.

Conveniently, the diester product (3) can be isolated from the reaction mixture as a solid which can be easily filtered off.

By using the preferred procedure, yields of above 80% can be routinely achieved. Advantageously, in the latter, preferred procedure it has been found that the diester product (3) can be isolated from the reaction mixture in high purity (typically greater than 95%, with greater than 99% being achievable). Also, the esterification reagent (e.g. isopropenyl acetate) is not corrosive.

The 6-halo compound of formula (4) can be produced from the diester (3) by reaction with a halogenating agent (e.g. bromine, or an N-halosuccinimide). A preferred halogenating agent in this step (ii) is an N-halosuccinimide (e.g. N-fluorosuccinimide, N-chlorosuccinimide, N-bromo-succinimide and N-iodosuccinimide, the latter two of which are preferred). Good results for this reaction have been achieved especially with N-bromosuccinimide (NBS) as the halogenating agent.

The halogenating agent is employed in a slight molar excess with respect to the diester starting material (3). Typically, amounts of 1.01 to 1.1 equivalents of the halogenating agent is employed.

In a typical procedure, the diester of formula (3) is contacted with the halogenating agent at a temperature range of 10° C. or less, preferably 0° C. or less. Especially preferred reaction temperatures are in the range of −20° C. to −5° C., with excellent results being obtained at −10° C. to −5° C. The mixture may then be allowed to warm to ambient temperature (e.g. 15° C. to 30° C., preferably 18° C. to 28° C.), preferably without application of a heating means the reaction may be suitably conducted in an aprotic solvent, such as dimethylformamide.

The 6-halo compound of formula (4) may then be isolated from the reaction mixture before carrying out the dehydrohalogenation step (iii). However, in a preferred procedure, steps (ii) and (iii) are carried out sequentially in one pot without isolating the 6-halo compound of formula (4).

In the dehydrohalogenation step, the compound of formula (4) [which may be present as a reaction mixture from step (3), or which may be in isolated form and dissolved in a suitable solvent such as dimethylformamide], is contacted with lithium carbonate and lithium halide (e.g. lithium chloride, lithium bromide and lithium iodide, with lithium bromide being especially preferred).

The dehydrohalogenation reaction may be carried out at a temperature of between 50 to 120° C., preferably 60 to 100° C. until completion of the reaction. A temperature range of between 70 to 90° C. is especially preferred.

Advantageously, the product can be isolated from the reaction mixture as a solid, which can be easily collected by filtration. The reaction product containing compound (5) can be purified by precipitation from an alcoholic solution (e.g. isopropanol) using water;

In accordance with the present invention, a key intermediate in the synthesis of tibolone, compound (6), can be converted to another useful intermediate in the synthesis of tibolone, namely the aromatic 3-ether derivative of formula (7). Thus, in a further aspect of the present invention, there is provided a process for the production of a compound of formula (7):

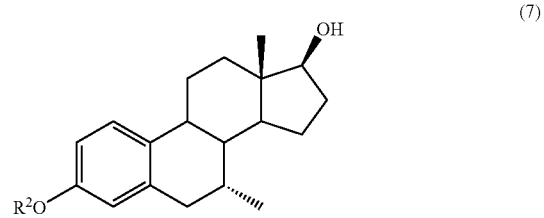

(7)

comprising the steps of:
(i) reacting the compound of formula (6):

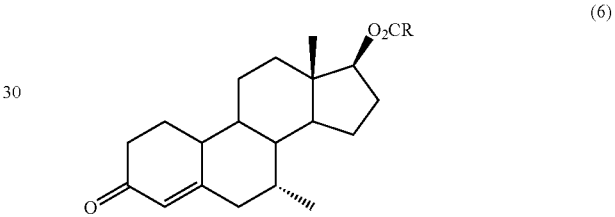

(6)

with a copper(II) salt in the presence of an alcohol $R^2$—OH wherein $R^2$ represents $C_1$ to $C_{10}$ alkyl, $C_6$ to $C_{10}$ aryl, $C_3$ to $C_6$ cycloalkyl, $C_7$ to $C_{20}$ aralkyl or $C_7$ to $C_{20}$ alkaryl to form a product mixture comprising a compound of formula (7); and optionally, (ii) contacting the product mixture with a base.

It is preferred that $R^2$ represents $C_1$ to $C_{10}$ (preferably $C_1$ to $C_6$) alkyl. Methyl is particularly preferred.

In this procedure, the A ring of the steroid skeleton is aromatised, the protecting group at the 17-position is removed and the 3-keto group is protected.

Interestingly, it is believed that the etherification of the 3-keto function occurs by an alkoxylation reaction, wherein $CH_3O^-$ from methanol acts as an alkoxylating agent. Advantageously, the above procedure for inter alia etherification of the 3-keto function does not require the use of traditional alkylating agents, such as the carcinogenic dimethylsulfate.

In the above procedure, a preferred copper(II) salt is copper (II) halide [e.g. copper(II) chloride, copper(II) bromide and copper(II) iodide, with copper(II) bromide being especially preferred]. The copper(II) salt is typically employed in an amount of 1.5 to 3 (preferably 2 to 2.5) molar equivalents with respect to the starting compound (6).

In this process, $R^2$ preferably represents a $C_1$ to $C_4$ alkyl group. In an especially preferred procedure, the alcohol employed is methanol (i.e $R^2$ represents methyl).

The alcohol $R^2$—OH is typically employed in excess, so that it performs an additional function of being a reaction solvent. A further solvent component such as toluene, xylene or acetonitrile may also be added.

The reaction may be conducted at a temperature in the range of 10° C. to 40° C. Good results can be obtained using reaction temperatures in the range of 15° C. to 30° C.

The reaction of the compound of formula (6) with copper (II) bromide [step (i)] under the conditions discussed above may lead to the formation of the side product (7*):

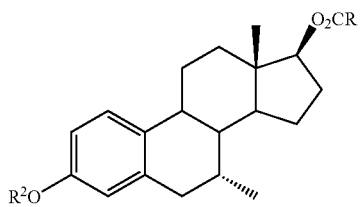

(7*)

The product (7*) is the 17-ester derivative of the desired compound of formula (7), and is typically present in the reaction mixture in relatively small quantities.

However, the compound of formula (7*) can be easily converted to the desired compound (7) by a saponification reaction. Thus, the compound of formula (7*) can be separated from the reaction mixture (e.g. by crystallisation) and contacted with any suitable base (e.g. sodium or potassium hydroxide). Alternatively, and more preferably, the compound of formula (7*) need not be isolated from the reaction mixture. Thus, the saponification reaction can be carried out on a mixture of compounds (7) and (7*).

In a typical procedure, any side product (7*) formed from the aromatisation reaction can be converted to the desired product (7) directly after the aromatisation step (after work up). Thus, after completion of the aromatisation reaction, the product mixture containing compound (7) and (7*) is extracted into an organic solvent (e.g. toluene). The organic extracts containing the compounds (7) and (7*) are extracted with an aqueous base solution (preferably potassium hydroxide). An alcohol solvent may also be added. The two phase mixture can then be heated to reflux temperature in order to saponify the ester in the compound (7*).

This one-pot procedure, i.e. wherein the saponification of compound (7*) is conducted without separation of (7) and (7*) is the method of choice.

The product (7) can advantageously be isolated from the saponification step by crystallisation (e.g. from toluene-alcohol mixtures—isopropanol being a preferred crystallisation co-solvent).

Yields of over 78% for the conversion of compound (6) to compound (7), including the saponification step can be achieved in accordance with the present process.

In another aspect of the present invention; there is provided a process for the production of a compound of formula (9):

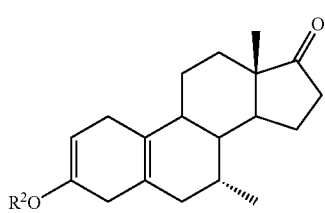

(9)

said process comprising reacting a compound of formula (8):

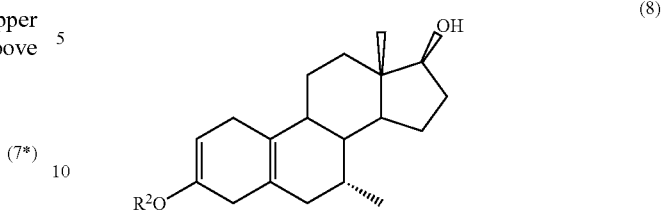

(8)

with an aluminium alkoxide, in the presence of a proton acceptor compound, e.g. aldehyde or ketone. Benzaldehyde is a particularly suitable aldehyde for this process. Cyclohexanone can also be used.

The compound of formula (9) is a further intermediate in the synthesis of tibolone.

In the above process according to the present invention, the 17-hydroxyl group of the starting material (8) (which can be synthesised by procedures described hereinafter), is oxidised to produce the corresponding 17-keto derivative (9).

Suitable aluminium alkoxide reagents that may be used in the conversion of compound (8) to compound (9) include those having the formula $Al(O-R^a)_3$ wherein at least one $R^a$ group contains a branched (e.g. $C_3$ to $C_{20}$, preferably $C_3$ to $C_{10}$) alkyl group (i.e. the alkyl group contains, for example, one or more secondary and/or tertiary alkyl groups), a cycloalkyl (e.g. $C_3$ to $C_7$) group or an aryl (e.g. $C_6$ to $C_{10}$) group. For example, the aluminium alkoxide reagent can include those having the formula:

$$Al(O-R^a)_3$$

wherein each $R^a$ can be the same or different and each represents a branched $C_3$-$C_{10}$ (preferably $C_3$ to $C_6$) alkyl group, a $C_6$ to $C_{10}$ aryl group, a $C_3$ to $C_7$ cycloalkyl group, a $C_7$ to $C_{20}$ aralkyl group or a $C_7$ to $C_{20}$ alkaryl group. Preferred are aluminium alkoxide reagents of the above formula wherein each $R^a$ is the same or different and each represents a $C_3$ to $C_6$ alkyl group. Preferably, each $R^a$ is the same. For example, $R^a$ can be selected from iso-propyl, tert-butyl and sec-butyl (1-methylpropyl).

Particularly preferred aluminium alkoxides include $Al(O^tBu)_3$ and $Al(^iPrO)_3$. $Al(O^tBu)_3$ is an especially preferred reagent.

The aluminium alkoxide reagent may be employed in an amount of 0.05 to 0.5, preferably 0.1 to 0.3, equivalents with respect to the starting material (8).

The reaction may be conveniently carried out at room temperature (i.e. in a temperature range of 15° C. to 30° C.).

It is preferred that the reaction is carried out in the presence of an ether solvent, such as an ether represented by the formula $R^b-O-R^c$, wherein $R^b$ and $R^c$ can be the same or different and each represents a $C_1$ to $C_8$ alkyl group. Preferably, $R^b$ and $R^c$ each represents a $C_1$ to $C_4$ alkyl group. A preferred ether solvent is tert-butyl methyl ether.

In the above procedure, any suitable aldehyde or ketone (e.g. benzaldehyde, cyclohexanone, etc.) may be employed as a proton acceptor compound. The identity of the aldehyde or ketone is not critical, as long as the compound can perform the function of a proton acceptor. An especially preferred proton acceptor comprises benzaldehyde. The proton acceptor, e.g. benzaldehyde, is preferably employed in an amount of between 1 to 3 equivalents with respect to the starting material (8). Good results have been achieved with amounts of 1 to 2 equivalents.

It has been found that the oxidation process proceeds even more smoothly when an antioxidant is added. Typical examples of antioxidant compounds include butylated hydroxytoluene (BHT or 2,6-di-tert-butyl-4-methylphenol) and butylated hydroxyanisole (BHA, which comprises a mixture of isomers: 3-tert-butyl-4-hydroxyanisole and 2-tert-butyl-4-hydroxyanisole), of which BHT is preferred. It is believed that the use of such antioxidants in this process inhibits potential aromatisation of the steroid A ring.

The product, compound (9) can be conveniently isolated as a solid from the reaction mixture by crystallisation. A particularly preferred method for the isolation of compound (9) from the reaction mixture employs an aqueous organic acid, such as lactic acid, which is added to the reaction mixture after completion of the reaction, to form a biphasic layer. After stirring for a period of from 10 minutes to 120 minutes, the organic layer can be separated, washed successively with aqueous sodium chloride and aqueous sodium hydrogencarbonate and water. The partial removal of the ether solvent followed by addition of methanol and then cooling allows facile and clean recovery of the product as a solid, which can be filtered off.

In the procedure disclosed in U.S. Pat. No. 3,340,279 discussed hereinabove, for the conversion of 7α-methyl-17β $\Delta^{2,5(10)}$-oestradiene to 7α-methyl-17-keto-3-methoxy-$\Delta^{2,5}$ $_{(10)}$-oestradiene, aluminium isopropylate and cyclohexanone are employed, and the reaction is conducted in toluene as the solvent. This prior art procedure requires steam distillation in order to isolate the product. The final product must be subsequently purified by chromatography over silica gel. Advantageously, in the present process for the conversion of compound (8) to compound (9), the final product can be isolated by simple extraction and filtration procedures, thus avoiding the need for chromatography.

The starting material for this process, compound (8), can be obtained from the intermediate methylether compound (7) by reduction under Birch conditions. The reaction involves a 1,4-addition of hydrogen:

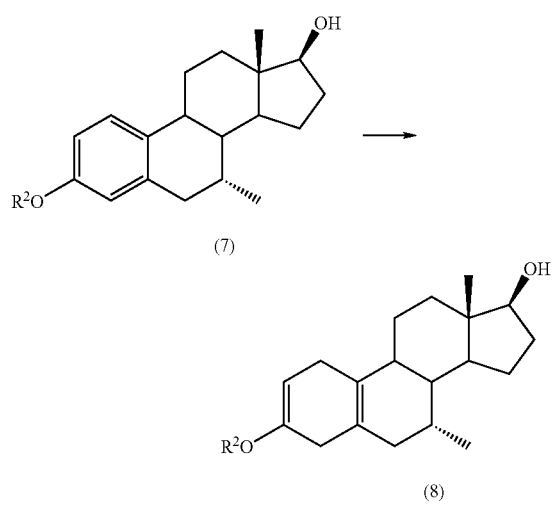

This conversion may be achieved using an alkali/alkaline earth metal in liquid ammonia, in the presence of a proton source. Suitable metals can include potassium, sodium, lithium and calcium. Particularly good results have been obtained using calcium metal. This has the advantage of being much easier to handle than, e.g. potassium, which is highly reactive.

The proton source is typically an alcohol. Any suitable (e.g. $C_1$ to $C_6$) alkylalcohol (e.g. methanol, ethanol, propanol, butanol, etc.) can be employed. The reaction is preferably carried out at low temperature, i.e. less than –10° C. Preferably, the reaction is conducted at a temperature range of between –70° C. to –20° C. Even more preferably, the reaction is conducted in a temperature range of 48° C. to –30° C.

Conveniently, the resulting-product, compound (8) can be isolated from the reaction mixture by extraction procedures. This procedure leads to high yields (typically above 70%) of the product.

In a further aspect of the present invention, there is provided a process for the production of a compound of formula (10):

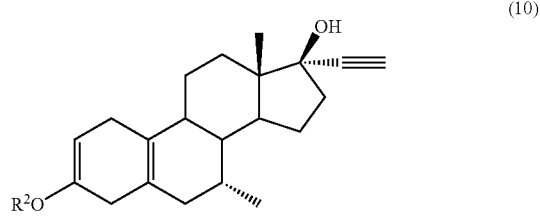

said process comprising subjecting the compound of formula (9):

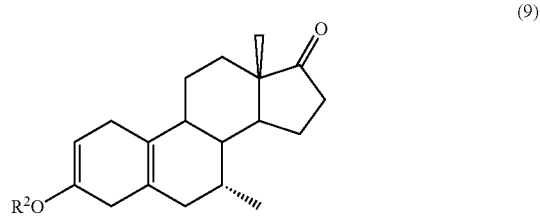

to reaction with an ethynylmagnesium halide (e.g. ethynylmagnesium chloride, ethynylmagnesium bromide and ethynylmagnesium iodide).

The compound of formula (10) is the precursor to tibolone.

Particularly preferred in this process of the present invention are ethynylmagnesium chloride and ethynylmagnesium bromide, which are commercially available, typically as solutions in tetrahydrofuran. The ethynylmagnesium halide is added in an amount of from 2.5 to 5 molar equivalents with respect to the starting material compound (9). Preferably, about 3 molar equivalents are employed.

The ethynylation procedure is typically carried out in the presence of an aprotic solvent, such as tetrahydrofuran.

Reaction temperatures of between 15° C. to 50° C. (preferably 20° C. to 40° C. and even more preferably 20° C. to 30° C.) can be employed.

Typically, the reaction mixture may be quenched with ammonium chloride and the product isolated by precipitation followed by filtration to produce a crude solid. After drying, the solid can be purified by crystallisation.

The ethynylation of compound (9) to form compound (10) may also be carried out by subjecting compound (9) to reaction with sodium acetylide.

When sodium acetylide is employed as the ethynylating agent, the reaction may be carried out in the presence of an antioxidant compound such as butylated hydroxytoluene (BHT) or butylated hydroxyanisole (BHA). The reaction may be carried out in any suitable aprotic solvent, particularly ether solvents, such as tert-butylmethyl ether and tetrahydrofuran. Preferably, the reaction is carried out in the presence of a solvent containing N-methylpyrrolidinone.

Sodium acetylide is available commercially as a solution in e.g. xylene. Sodium acetylide is preferably added in an amount of from 2 to 3 molar equivalents, preferably 2 to 2.5 molar equivalents with respect to the starting compound (9).

Reaction temperatures of between 10° C. to 40° C. (preferably 15° C. to 30° C. and even more preferably 20° C. to 25° C.) can be employed.

Typically, the reaction mixture may be quenched with ammonium chloride and the product isolated by precipitation followed by filtration to produce a crude solid. After drying, the solid can be purified by crystallisation.

The ethynylation procedures described-above have several advantages over the prior art procedures. In particular, U.S. Pat. No. 3,340,279 discloses the use of potassium acetylide as the ethynylating agent. Potassium acetylide is formed by reaction of potassium metal with acetylene. The use of potassium, which is highly reactive, is not recommended for large scale synthesis in view of safety. Further, the product 7α-methyl-17α-ethynyl-17β-hydroxy-3-keto-Δ$^{5(10)}$-oestrene must be isolated by a relatively more complex procedure involving steam distillation and chromatography over silica gel.

In the procedure disclosed in Van Vliet et al., in Recl. Trav. Chim. Pays-Bas, 105, 111-115 (1986), the ethynylation of 3,3-dimethoxy-7α-methylestr-5(10)-en17-one to form the corresponding 3,3-dimethoxy-7α-methyl-19-nor-17'-preg-5(10)-en-20-yn-17β-ol is achieved using potassium tert-butoxide and acetylene. Again, the use of these flammable and explosive reagents is not advised in large scale operations.

In a further aspect of the present invention there is provided a process for the production of tibolone (11):

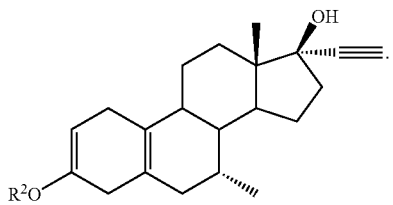

(10)

The mineral acid is preferably selected from sulfuric acid, nitric acid and hydrochloric acid. Aqueous hydrochloric acid is a particularly preferred reagent.

The mineral acid is generally in a dilute aqueous solution. Preferably the mineral acid is employed as a aqueous solution at a concentration range of 0.05 M to 0.5 M, more preferably about 0.1 M. The reaction is typically conducted in a solvent comprising a $C_1$ to $C_6$ alcohol (e.g. methanol, ethanol, propanol or butanol; ethanol is preferred).

Hitherto, prior art procedures for the deprotection of the 3-keto group have employed organic acids, usually oxalic acid in a mixture of water and methanol.

Unexpectedly, it has been found that the purity of the final product may be improved by the addition of a small amount of an antioxidant compound (such as ascorbic acid) to an alcoholic solution of the starting material before the addition of the mineral acid. The antioxidant (e.g. ascorbic acid) may be added to the reaction mixture as a solution in ethanol, in an amount of from 0.1 to 1% w/w (preferably 0.3-0.7% w/w) with respect to the starting material (10).

In a further aspect of the present invention, there is provided a process for the synthesis of tibolone (11):

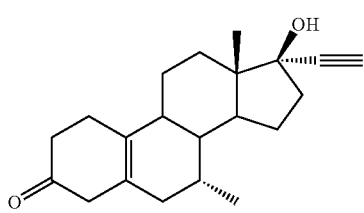

(11)

said process comprising deprotecting the hydroxyl protecting group of a compound of formula (10) with a mineral acid In general terms, the process for the synthesis of tibolone in accordance with the present invention is shown in the following scheme:

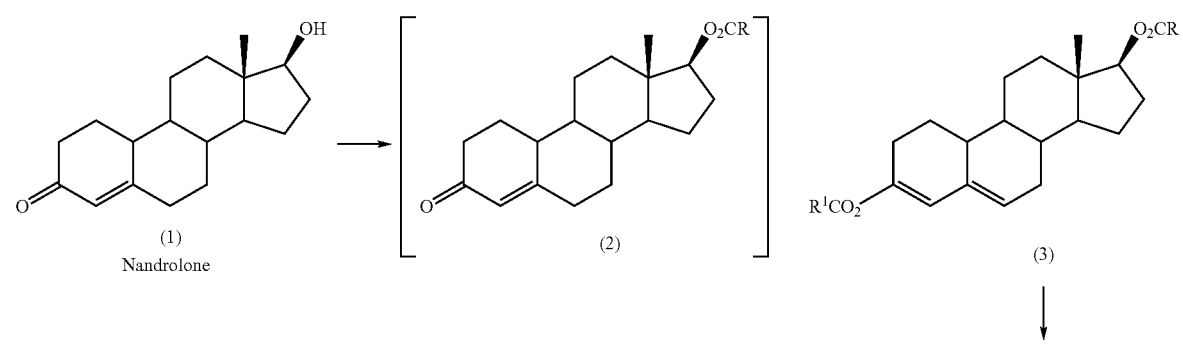

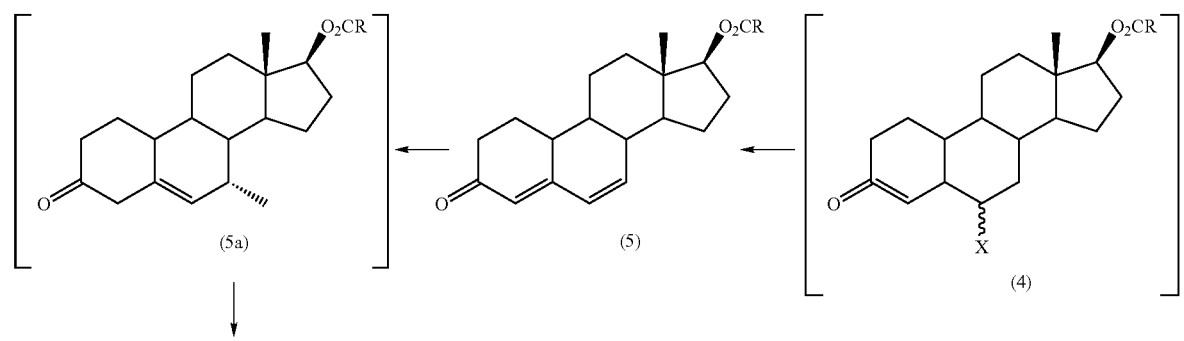
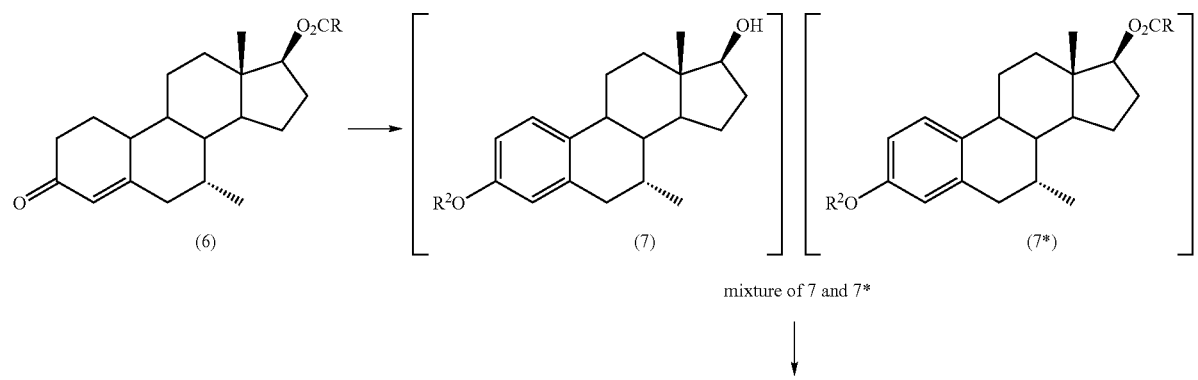
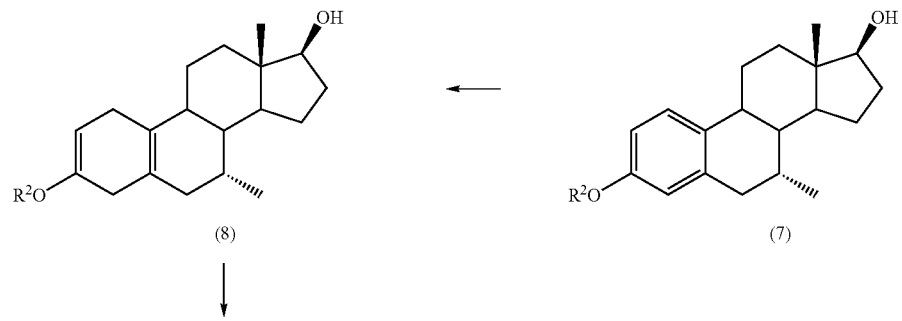
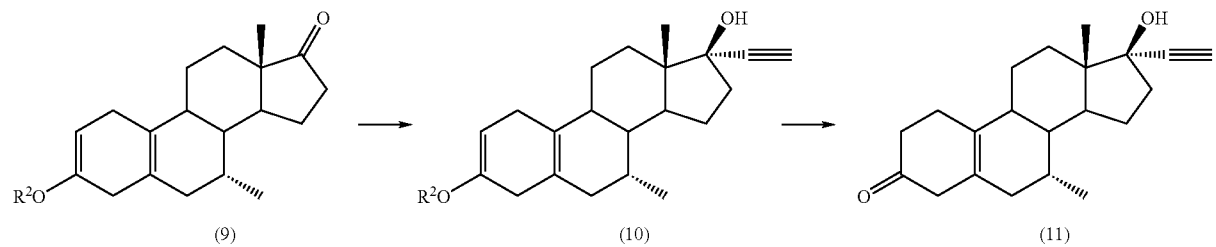

Thus, according to this aspect of the present invention, there is provided a process for the synthesis of tibolone from nandrolone (1)

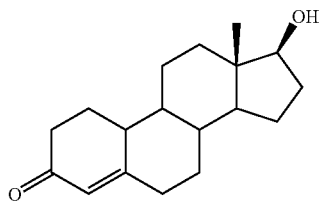
(1)

said process comprising the steps of:

(i) protecting the 17-hydroxy group and the 3-keto group of nandrolone (1) to produce a compound of formula (3):

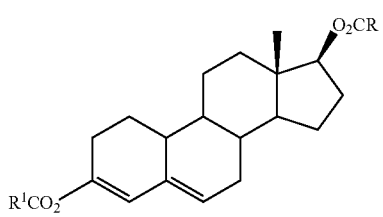
(3)

wherein R and $R^1$ may be the same or different and each independently represents: $C_1$ to $C_{20}$ alkyl, $C_6$ to $C_{10}$ aryl, $C_3$ to $C_8$ cycloalkyl, $C_7$ to $C_{20}$ aralkyl, or $C_7$ to $C_{20}$ alkaryl (preferably R and $R^1$ each represents $C_1$ to $C_{20}$ alkyl, with $C_1$ to $C_6$ alkyl, especially methyl, being particularly preferred);

(ii) halogenating the carbon at the 6-position of the compound of formula (3) using a halogenating agent, to produce a compound of formula (4);

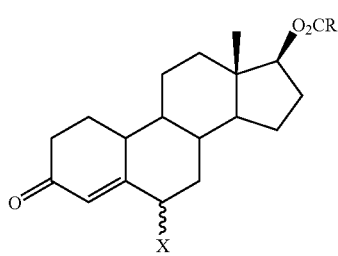
(4)

wherein X represents F, Cl, Br or I;

(iii) dehydrohalogenating the compound of formula (4) to produce a compound of formula (5):

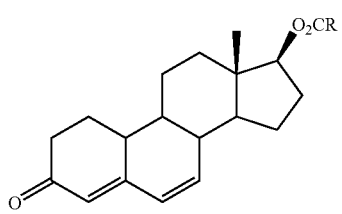
(5)

(iv) methylating the carbon atom at the 7-position of the compound of formula (5) to produce a compound of formula (5a):

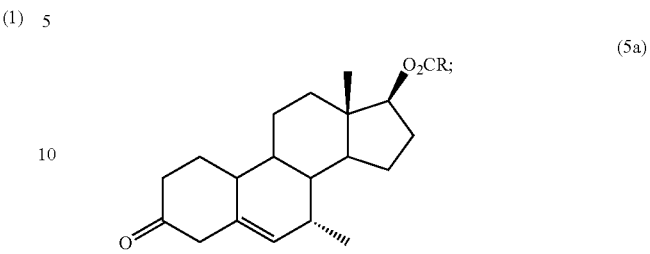
(5a)

(v) isomerising the C=C double bond of the compound of formula (5a) to produce a compound of formula (6):

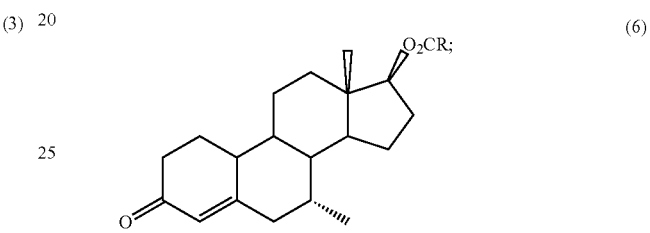
(6)

(vi) dehydrogenating the compound of formula (6) using $CuBr_2$ in the presence of an alcohol, $R^2$—OH to produce a compound of formula (7):

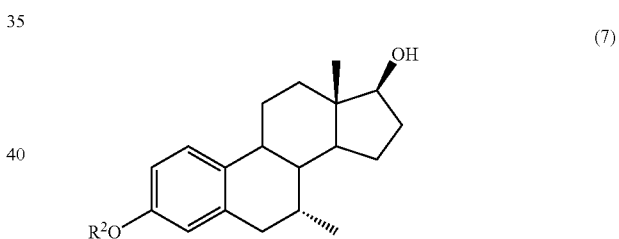
(7)

wherein $R^2$ represents. $C_1$ to $C_{20}$ alkyl, $C_6$ to $C_{10}$ aryl, $C_3$ to $C_8$ cycloalkyl, $C_7$ to $C_{20}$ aralkyl or $C_7$ to $C_{20}$ alkaryl (preferably $R^2$ represents $C_1$ to $C_6$ alkyl, with methyl being especially preferred); and optionally contacting the product mixture with a base (such as aqueous potassium hydroxide), as discussed hereinabove, in order to convert any co-formed compound of formula (7*) to the desired compound (7);

(vii) reducing the compound of formula (7) to produce a compound of formula (8):

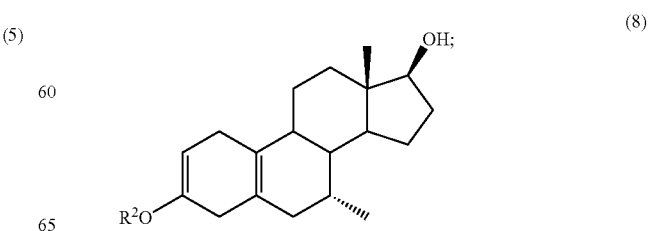
(8)

(viii) oxidising the 17-hydroxyl group of the compound of formula (8) to produce a compound of formula (9):

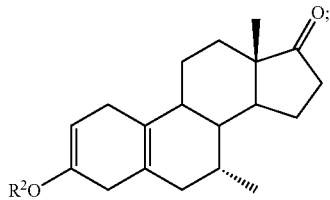

(ix) ethynylating the carbon at the 17-position of the compound of formula (9) to produce a compound of formula (10):

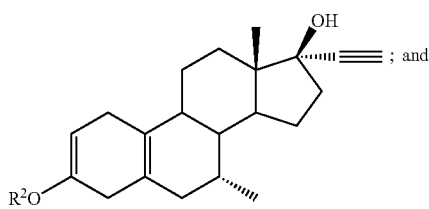

(x) removing the protecting group $R^2$ in the compound of formula (10) to produce tibolone (11):

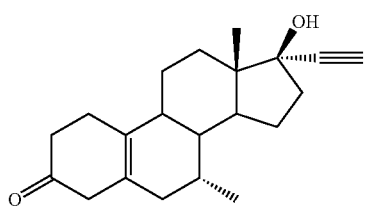

Step (i) can comprise the following steps (a) and (b):

(a) reacting nandrolone (1) with an alkanoylating agent having the formula $(RCO)_2O$ wherein R represents: $C_1$ to $C_{20}$ alkyl, $C_6$ to $C_{10}$ aryl, $C_3$ to $C_8$ cycloalkyl, $C_7$ to $C_{20}$ aralkyl, or $C_7$ to $C_{20}$ alkaryl (preferably R represents $C_1$ to $C_{20}$ alkyl, with $C_1$ to $C_6$ alkyl, especially methyl, being particularly preferred), to produce a compound of formula (2);

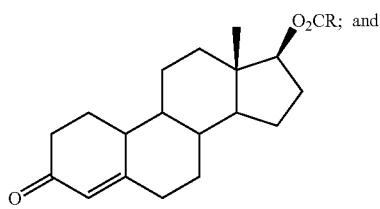

(b) reacting the compound of formula (2) with an acetylating agent having the formula $R^1$—CO—X wherein $R^1$ represents: $C_1$ to $C_{20}$ alkyl, $C_6$ to $C_{10}$ aryl, $C_3$ to $C_8$ cycloalkyl, $C_7$ to $C_{20}$ aralkyl, or $C_7$ to $C_{20}$ alkaryl (preferably $R^1$ represents $C_1$ to $C_{20}$ alkyl, with $C_1$ to $C_6$ alkyl, especially methyl, being particularly preferred), and X represents halo (preferably Cl, Br, I, with Cl being particularly preferred).

Preferably, step (i) comprises reacting nandrolone (1) with a compound of formula:

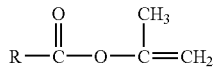

wherein R represents: $C_1$ to $C_{20}$ alkyl, $C_6$ to $C_{10}$ aryl, $C_3$ to $C_8$ cycloalkyl, $C_7$ to $C_{20}$ aralkyl, or $C_7$ to $C_{20}$ alkaryl (preferably R and $R^1$ each represents $C_1$ to $C_{20}$ alkyl, with $C_1$ to $C_6$ alkyl, especially methyl, being particularly preferred), in the presence of para-toluene sulfonic acid.

Step (ii) preferably comprises reacting the compound of formula (3) with an N-halosuccinimide, wherein halo preferably represents F, Cl, Br or I (N-bromosuccinimide is especially preferred).

Step (iii) preferably comprises reacting the compound of formula (4) with lithium halide and lithium carbonate.

Step (iv) preferably comprises reacting the compound of formula (5) with methyl-magnesium halide (preferably, the halide is chloride, bromide or iodide, with chloride being particularly preferred) in the presence of copper(II) acetate.

Step (v) preferably comprises reacting the compound of formula (6) with an aqueous mineral acid (e.g. hydrochloric acid).

Step (vi) preferably includes the step of contacting the product mixture from the aromatisation reaction with a base (preferably aqueous potassium hydroxide) in order to convert co-formed compound (7*) to the desired product (7).

Step (vii) preferably comprises reacting the compound of formula (7) with calcium and liquid ammonia.

Step (viii) preferably comprises reacting the compound of formula (8) with an aluminium alkoxide reagent in the presence of an aldehyde or ketone proton acceptor (e.g. benzaldehyde). The aluminium alkoxide reagent has a formula $Al(O-R^a)_3$, wherein at least one $R^a$ group contains a branched (e.g. $C_3$ to $C_{20}$, preferably $C_3$ to $C_{10}$) alkyl group (i.e. the alkyl group contains, for example, one or more secondary and/or tertiary alkyl groups), a cycloalkyl (e.g. $C_3$ to $C_7$) group or an aryl (e.g. $C_6$ to $C_{10}$) group. For example, the aluminium alkoxide reagent can include those having the formula:

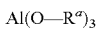

wherein each $R^a$ can be the same or different and each represents a branched $C_3$-$C_{10}$ (preferably $C_3$ to $C_6$) alkyl group, a $C_6$ to $C_{10}$ aryl group, a $C_3$ to $C_7$ cycloalkyl group, a $C_7$ to $C_{20}$ aralkyl group or a $C_7$ to $C_{20}$ alkaryl group. Preferred are aluminium alkoxide reagents of the above formula wherein each $R^a$ is the same or different and each represents a $C_3$ to $C_6$ alkyl group. Preferably, each $R^a$ is the same. For example, $R^a$ can be selected from iso-propyl, tert-butyl, sec-butyl (1-methylpropyl). Preferably, step (viii) comprises reacting the compound of formula (8) with $Al(^iPrO)_3$ or $Al(O^tBu)_3$ in the presence of benzaldehyde. As indicated hereinabove, an antioxidant compound, such as BHT or BHA is preferably added to the reaction mixture in step (viii).

Step (ix) preferably comprises reacting the compound of formula (9) with ethynylmagnesium halide (wherein the halide is preferably chloride or bromide, with chloride being particularly preferred). Step (ix) may also conveniently be carried out by reacting the compound of formula (9) with sodium acetylide.

Step (x) preferably comprises contacting the compound of formula (10) with aqueous mineral acid, preferably aqueous hydrochloric acid.

Preferred conditions and reagents for steps (i) to (x) have been described hereinabove.

In any of the processes and intermediates described herein, preferably the groups R, $R^1$ and $R^2$ each independently represent $C_1$ to $C_6$ alkyl, with $C_1$ to $C_3$ alkyl being particularly preferred. Even more preferred are processes as defined in any of the preceding paragraphs wherein R, $R^1$ and $R^2$ each independently represents unsubstituted $C_1$ to $C_6$ (preferably $C_1$ to $C_3$) alkyl. Particularly preferred are processes as described in any of the preceding paragraphs wherein R, $R^1$ and $R^2$ each represents methyl.

The invention will be further illustrated by the following examples.

EXAMPLES

The following examples illustrate processes according to the present invention. As a precaution, reactions were conducted under a nitrogen atmosphere.

Example 1

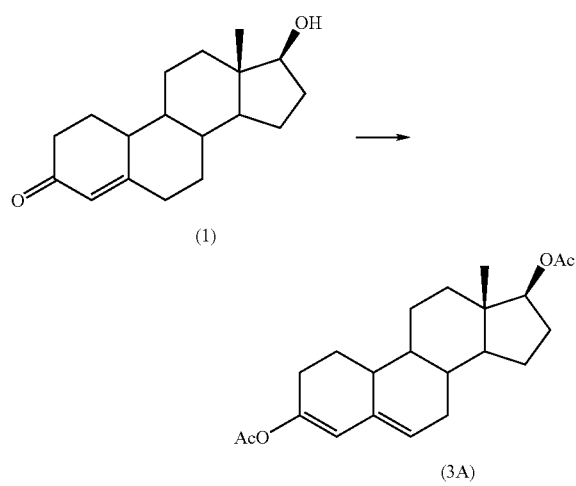

Isopropyl acetate (0.785 kg), nandrolone (1) (0.200 kg), and a catalytic amount of p-toluenesulfonic acid monohydrate (0.007 kg) were combined at ambient temperature under nitrogen. The suspension was stirred and heated to reflux. Isopropenyl acetate (0.236 kg) was then added drop wise, over a 10-30 minute period and reflux was continued. The reaction was monitored at 60 minute intervals by HPLC analysis until completed. Upon completion, 2 volumes (with respect to the weight of nandrolone input) of solvent were removed from the mixture by distillation at atmospheric pressure. The reaction mixture was cooled to 75-78° C. and triethylamine (0.005 kg) was added. The mixture was cooled to 75° C. and isopropanol (0.314 kg) was added. After completion of the addition, the mixture was cooled to between –5 and –15° C. and the product-isolated by filtration. The product was washed on the filter with chilled isopropanol, and dried in a vacuum oven to constant weight (yield 85%).

Example 2

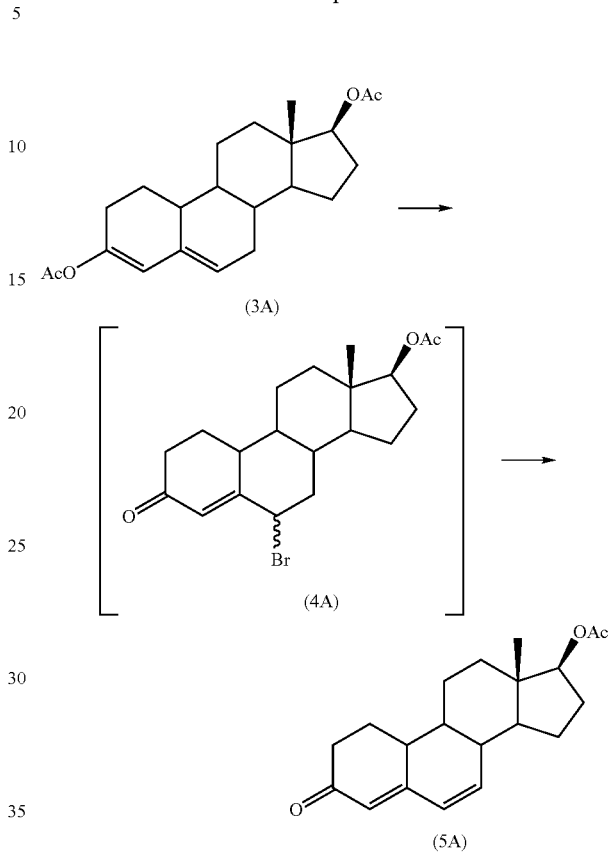

To a suspension of compound (3A) (0.200 kg) in DMF (0.755 kg) and water (0.0124 kg) at –10° C. to –5° C. was added a solution of N-bromosuccinimide (0.107 kg) in dimethylformamide (DMF) (0.330 kg) drop wise over 2 hours whilst maintaining the temperature below 0° C. The reaction mixture was allowed to warm to 20 to 25° C. over a 30 minute period and monitored by HPLC. Upon completion of the reaction, lithium carbonate (0.099 kg) and lithium bromide (0.051 kg) were added sequentially with thorough stirring. The reaction mixture was slowly heated to 80° C. over 1 hour and maintained at 80±5° C. for 2 to 3 hours until the reaction was complete. Heating was then stopped and the beige/brown suspension was cooled to 20 to 25° C. The mixture was quenched by the drop wise addition of aqueous acetic acid (0.177 kg in 1.11 kg water). Shortly after the addition commenced, the mixture was seeded with compound (5A) (0.001 kg). Finally, the remaining aqueous acetic acid was added and the mixture was stirred at room temperature overnight. The solid was isolated by filtration and the filter cake was washed initially with a 1:1 mixture of DMF and purified water (0.142 kg DMF in 0.150 kg water), and finally with purified water (3×0.200 kg). The crude solid was suspended in isopropanol (0.365 kg) and heated to 45° C. to form a brown solution. Purified water was added drop wise over a period of at least 30 minutes to precipitate the product. The slurry was cooled to 0 to 5° C. over 1 hour and was stirred at this temperature for 1 hour. The product was isolated by filtration and filter cake was washed with a cold (0 to 5° C.) mixture of isopropanol (0.04 kg) and purified water (0.060 kg) to give a pale yellow coloured powder. The purified solid was dried to constant weight under vacuum at 40 to 50° C. (yield: 79%).

Example 3

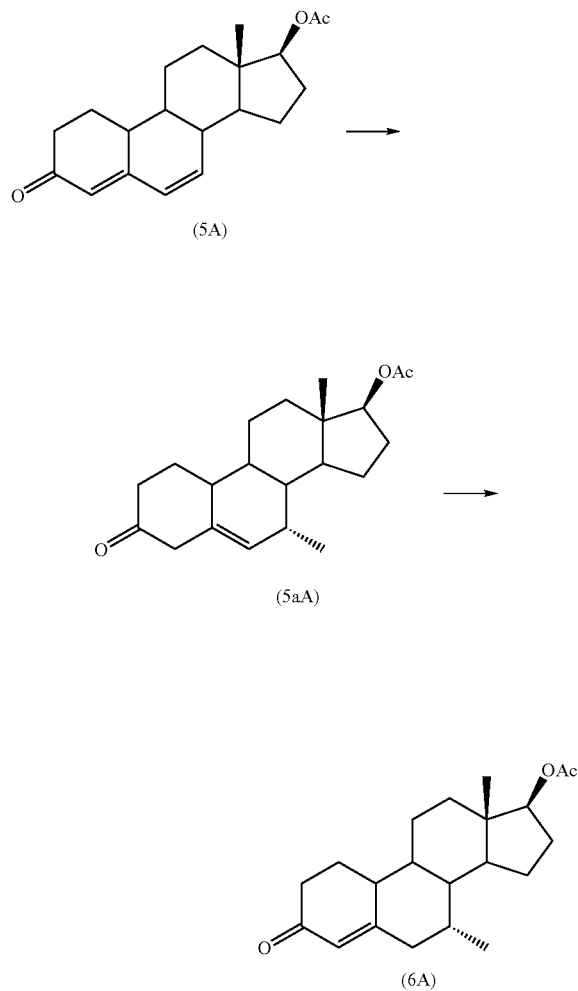

Tetrahydrofuran (717.6 g), compound (5A) (204 g) and anhydrous copper (II) acetate (23.6 g) were charged to a suitable vessel. The slurry was stirred and cooled to between −45° C. and −35° C. Methyl-magnesium chloride solution (23% in THF, assayed 22.6%, 346.1 g) was then added slowly at such a rate to maintain the reaction temperature between −45° C. and −35° C. over a minimum of three hours. After completion of the addition, the reaction mixture was stirred at −45° C. to −35° C. and monitored by HPLC. The mixture was then quenched with 37% hydrochloric acid (128.1 g) keeping the temperature below 10° C. The mixture was maintained below 10° C. for 30 minutes. Water (408 g) was slowly added over a period of about 20 minutes. Heptane (428.2 g) was added and the mixture allowed to warm to ambient temperature. The aqueous layer was separated and the product was extracted with heptane. The combined organic extracts were washed with 25% ammonium hydroxide solution and purified water. The solvent was distilled under atmospheric pressure until approximately 3 volumes [with respect to the input weight of compound (5A)] remained. Tert-butyl methyl ether was added and the mixture cooled to crystallise the product. The product was isolated by filtration and dried at 40-50° C. (yield: 78%; α:β ratio=99).

Example 4

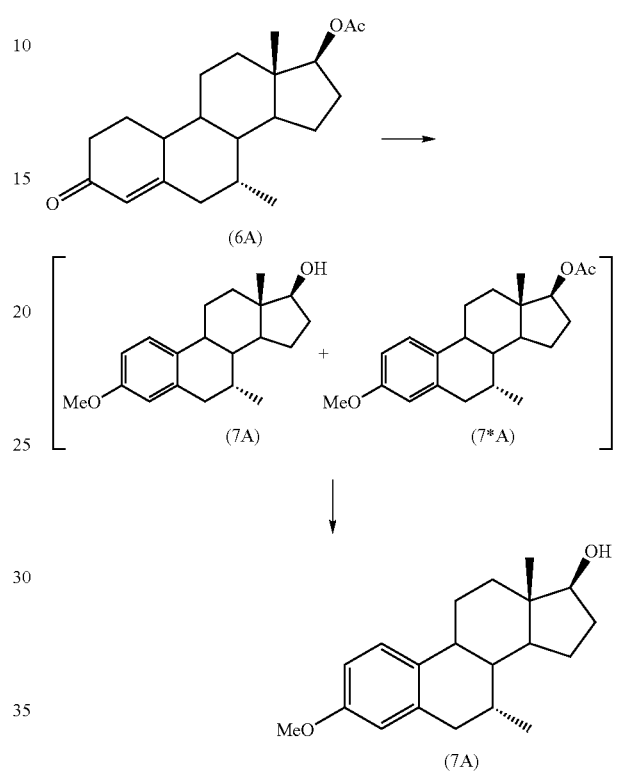

A solution of compound (6A) (52.35 kg) in toluene/methanol (87.0 kg toluene in 121.0 kg methanol) under nitrogen was treated with 2.2 molar equivalents of copper(II) bromide (75.09 kg) in portions at 17-23° C. Upon completion of reaction, the mixture was diluted with toluene (132 kg) and cooled to about 15° C. Aqueous sulphuric acid (351.0 kg) was added. The three-phase mixture was filtered to remove copper (I) salts and the organic phase was separated. The organic phase was washed with 14% aqueous sulfuric acid and 13% aqueous sodium chloride. The organic layer was separated and aqueous potassium hydroxide (50%, 12.1 kg) and methanol (20.5 kg) were added to the toluene phase. The two-phase mixture was heated to reflux until HPLC indicated complete conversion of compound (7*A) to compound (7A). Purified water (35 kg) was added and the aqueous phase was separated. The toluene solution was washed with aqueous disodium EDTA (12.0 kg in 230.0 kg water). The organic phase was concentrated at atmospheric pressure until the volume of solvent in the pot residue was 2 v/w with respect to the input of compound (6A). Isopropanol (276 kg) was added and the distillation continued until the volume in the reaction pot was again 2 v/w with respect to the input of compound (6A). Isopropanol (118.0 kg) was then added and the mixture heated to reflux. The solution was cooled slowly to induce crystallisation. The resulting suspension was cooled to 2 to 5° C. for 1.5 hours. The solid was filtered and the filter cake washed with isopropanol (2 to 5° C.). The product was dried at 55-60° C./50-100 mbar to constant weight (and until the isopropanol content is less than 5.0% w/w (yield: 80%).

Example 5

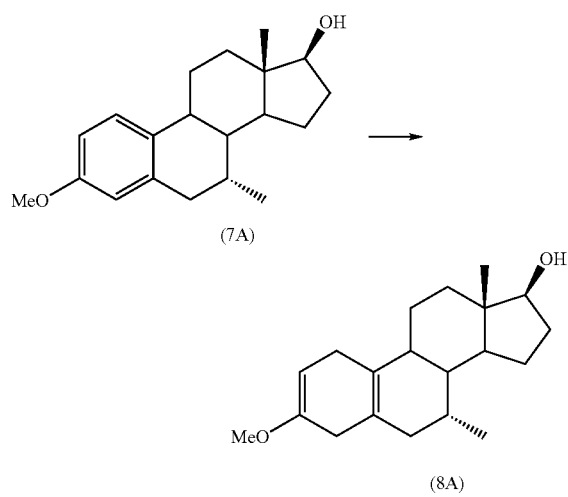

Liquid ammonia (383.51 g) was added a reaction vessel containing a slurry of compound (7A) (150 g), in tetrahydrofuran (266.70 g), tert-butyl methyl ether (888 g) and 2-propanol (235.5 g) at −38±5° C. Calcium metal (60.12 g) was then added portion-wise and the reaction mixture was stirred at −38±5° C. until the blue coloration dissipated completely. The reaction is monitored by HPLC. On completion, the reaction was quenched by addition of ammonium chloride (179.51 g) and then warmed to −10 to 0° C. Any ammonia distilled was trapped in a water scrubber. Water (1.2 kg) was added to the resulting off-white suspension and the mixture was warmed to ambient temperature. The organic layer was separated and the aqueous layer was re-extracted with heptane. The combined organic extracts were washed with 5% w/v aqueous ammonium chloride solution, 1% w/v aqueous sodium hydrogen carbonate and water. The organic phase was concentrated under reduced pressure down to 6 volumes with respect to the weight of compound (7) input. A mixture of heptane (153.9 g) and tert-butanol (58.5 g) was added and distillation was continued until level of tert-butyl methyl ether was ≦12.5% w/w. The resulting suspension was chilled to 0-5° C., filtered and the product washed with heptane and dried at 25-30° C. to constant weight (yield: 75%).

Example 6

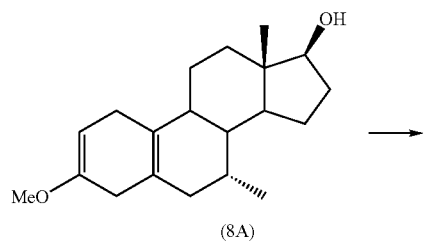

-continued

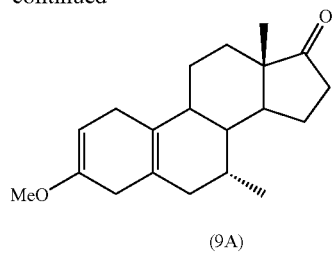

Tert-butyl methyl ether (222.0 g), 2,6-di-tert-butyl-4-methylphenol (0.50 g), compound (8A) (50 g) and benzaldehyde (26.3 g) were combined at ambient temperature and vacuum degassed with nitrogen. Aluminium tri-tert-butoxide (8.14 g) was then added and the hazy solution stirred for 60 minutes. The reaction was sampled after this period and then at 30 minute intervals until complete by HPLC analysis. Once complete, an aqueous solution of lactic acid (16.92 g in 250 g water) was added and the resulting biphasic solution stirred for at least 15 minutes. The organic layer was separated, washed successively with a 5% w/w solution of sodium chloride (263.2 g), 5% w/v solution of sodium hydrogen carbonate (105.0 g) and finally with water. The solution was concentrated by distillation until 2 volumes of methyl tert-butyl ether had been collected with respect to the input weight of compound (8A). Methanol (197.8 g) was then added and distillation continued until a further 5 volumes [with respect to the input weight of compound (8A)] of distillate had been collected. The solution was then cooled to 46-54° C. and crystallisation initiated. The suspension was then chilled at 0 to −5° C. for a further 60 minutes. The product was isolated by filtration, washed firstly with methanol, and secondly with aqueous methanol. The product was dried in the vacuum oven to constant weight (yield: 84.5%).

Example 7A

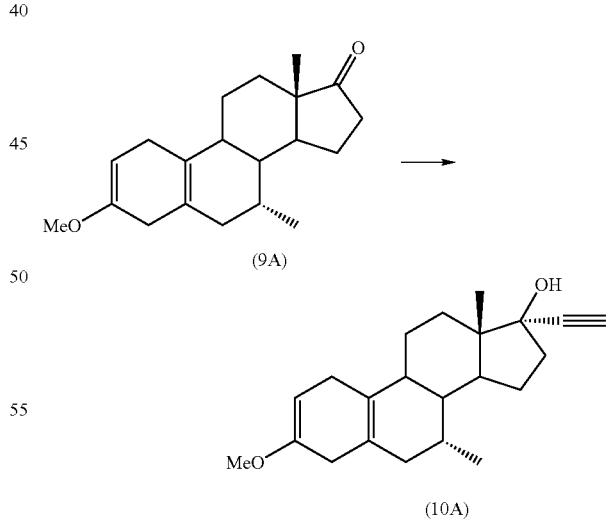

Stage 1

Compound (9A) (30.0 g) was dissolved in tetrahydrofuran (90 mL) at ambient temperature under nitrogen. This solution was added to a vacuum degassed solution of ethynyl magnesium chloride in tetrahydrofuran (325 mL, d=0.921, molarity 0.48 M) at 25-30° C. under nitrogen over at least 30 minutes.

The reaction mixture was stirred at 25-30° C. until completed, as assessed by HPLC. The reaction mixture was transferred under nitrogen to a 13% w/w solution of ammonium chloride in water (300 mL) at a rate to maintain the temperature of the quench mixture between 20-30° C. Celite (6.0 g) was then added to the biphasic reaction mixture which was then stirred for 30 minutes at 30±2° C. The resultant slurry was filtered and the upper organic layer was separated. The organic layer was washed with 30% w/w sodium chloride solution (150 mL). The organic solution was concentrated under reduced pressure to 6 volumes based on the compound (9A) input weight. Deionised water was added dropwise to complete the precipitation and the resultant slurry was cooled to 0-5° C. and stirred for at least one hour. The solid was collected by filtration. The filter cake was washed with a 1:1 mixture of THF/water and finally with water and pyridine solution. The solid was dried in the vacuum oven at 30-35° C. under vacuum until the water content was below 5% as judged by Karl Fischer titration.

Stage 2

The crude dried solid (33.9 g) from Stage 1 was dissolved in a mixture of methanol (160 mL) and pyridine (0.38 mL) at 55±2° C. under nitrogen to form a clear solution. Water (14 mL) was added dropwise at 55±2° C. and the mixture cooled. Crystallisation occurred at 50±5° C. The slurry was cooled to 0 to 5° C. and stirred at this temperature for at least one hour. The solid was isolated by filtration and dried at 30-35° C. under vacuum to constant weight (yield: 82%).

Example 7B

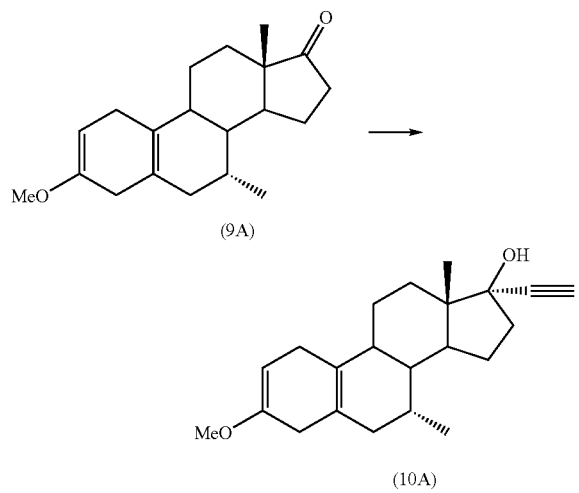

(9A)

(10A)

Stage 1

Compound (9A) (30 g) and 2,6-Di-tert-butyl-4-methyl phenol (BHT) (0.15 g) were dissolved in a vacuum degassed mixture of tert-butylmethyl ether (111 g) and N-methyl pyrrolidinone (45.9 g) at ambient temperature under nitrogen. This solution was added to a vacuum degassed slurry of sodium acetylide (21% w/w in xylene, 50.05 g) in N-methyl pyrrolidinone (107.1 g) at 20-25° C. under nitrogen over at least 30 minutes. The reaction was stirred at 20-25° C. for 2 hours after which an aliquot of water (0.18 g) was added. The mixture was stirred for a further hour and then analysed by HPLC. Further portions of water (2×0.18 g) were added until the reaction was complete as assessed by HPLC. The reaction mixture was transferred under nitrogen to a 13% w/w solution of ammonium chloride in water (19.5 g ammonium chloride and 130.5 g water) at such a rate to maintain the temperature of the quench mixture between 20-30° C. Celite (3 g) was then added to the biphasic reaction mixture and the mixture stirred for 15 minutes at 20-25° C. The resultant slurry was filtered and the upper organic layer was separated. The organic layer was washed twice with water (2×90 g). A trace of pyridine (0.16 g) was added to the organic solution and the mixture was concentrated under reduced pressure to 4 volumes with respect to the weight of the compound (9A) input. Water (30 g) and methanol (118.5 g) containing a trace of pyridine (0.16 g) were added and the reduced pressure distillation was continued until concentrated to 4 volumes with respect to the weight of the compound (9A) input. A further portion of methanol (118.5 g) and pyridine (0.16 g) was added and the mixture concentrated to 4 volumes with respect to the weight of the compound (9A) input. Deionised water (15 g) was added dropwise to complete the precipitation and the resultant slurry was cooled to 0 to −5° C., stirred for at least one hour, and then the solid was collected by filtration. The cake was washed with a chilled 50% mixture of methanol and water (120 mL). The solid was dried in a vacuum oven at 35° C. under vacuum until the water content was less than 6.3% w/w.

Stage 2

The crude dried solid from Stage 1 (10 g) was dissolved in a mixture of methanol (36.1 g) and pyridine (0.11 g) at 55±5° C. under nitrogen to form a clear solution. Water (3.93 g) was added dropwise at 55±5° C. and then the mixture cooled. Crystallisation occurred at 50±5° C. The slurry was cooled to 0 to 5° C. and stirred at this temperature for at least one hour. The solid was isolated by filtration and dried at 30-35° C. under vacuum until the water content was 2.4% or less.

Example 8

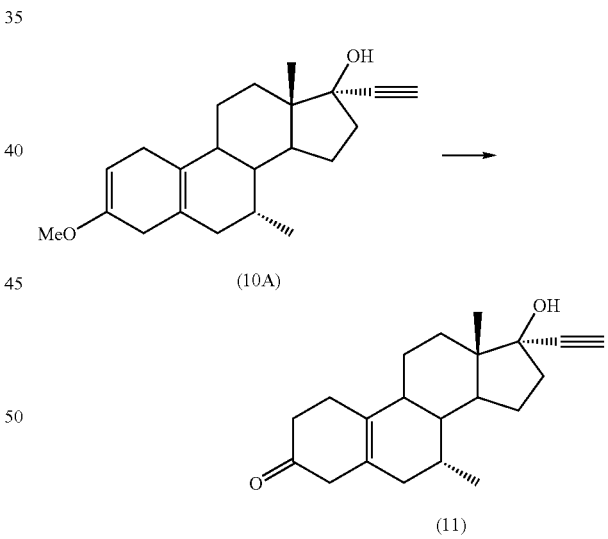

(10A)

(11)

Activated Carbon Darco G60 (3.90 g) was added to a degassed solution of compound (10A) and ascorbic acid (99%, 195 mg) in ethanol (96%, 658 g). The suspension was stirred under nitrogen for one hour at 20-30° C. and clarified by filtration. To the resulting clear solution, water (13.3 mL) and hydrochloric acid (0.1N, 29.64 g) were added, with stirring under nitrogen. The reaction was maintained at 20-25° C. and monitored by HPLC; additional charges of hydrochloric acid were added as necessary until the reaction was complete. On completion, aqueous potassium acetate (0.1M, 585 mL) was added to quench the reaction. The reaction mixture was then cooled to 0-5° C. for 1 hour. The resulting suspension was filtered and the filter cake washed with water. The product (11) was dried under vacuum at 30-35° C. to constant weight (yield: 78%).

The invention claimed is:
1. A process for the synthesis of tibolone (11):

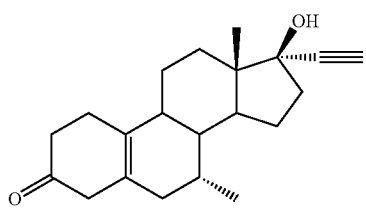

said process comprising the steps of:
(i) protecting the 17-hydroxy group and the 3-keto group of nandrolone (1)

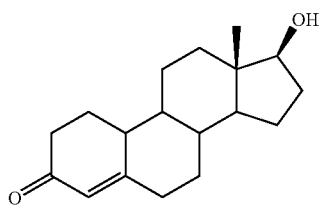

to produce a compound of formula (3):

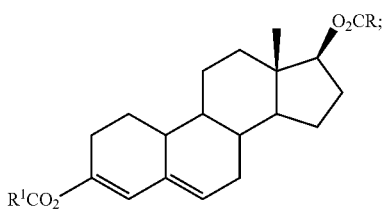

wherein R and $R^1$ may be the same or different and each independently represents: $C_1$ to $C_{20}$ alkyl, $C_6$ to $C_{10}$ aryl, $C_3$ to $C_8$ cycloalkyl, $C_7$ to $C_{20}$ aralkyl, or $C_7$ to $C_{20}$ alkaryl;
(ii) halogenating the carbon at the 6-position of the compound of formula (3) to produce a compound of formula (4);

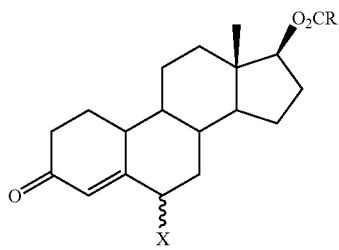

wherein X represents F, Cl, Br or I;

(iii) dehydrohalogenating the compound of formula (4) to produce a compound of formula (5):

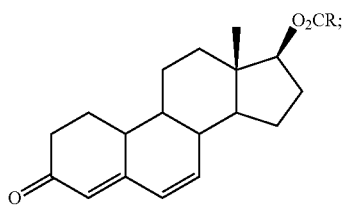

(iv) methylating the carbon atom at the 7-position of the compound of formula (5) to produce a compound of formula (5a):

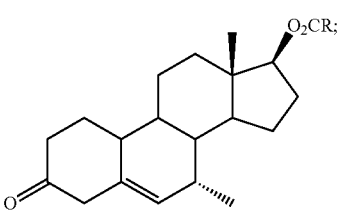

(v) isomerizing the C=C double bond of the compound of formula (5a) to produce a compound of formula (6):

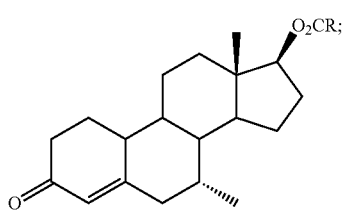

(vi) (a) dehydrogenating at a temperature of 15° C. to 30° C. the compound of formula (6) using $CuBr_2$ in the presence of an alcohol, $R^2$—OH to produce a product mixture comprising a compound of formula (7) and a compound of formula (7*):

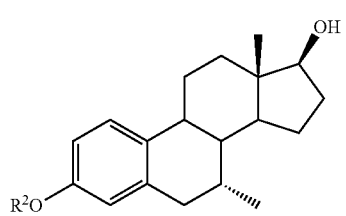

-continued

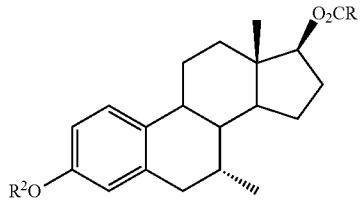
(7*)

wherein R² represents C₁ to C₁₀ alkyl, C₆ to C₁₀ aryl, C₃ to C₆ cycloalkyl, C₇ to C₂₀ aralkyl or C₇ to C₂₀ alkaryl;
and (b) optionally contacting the product mixture with a base;

(vii) reducing the compound of formula (7) to produce a compound of formula (8):

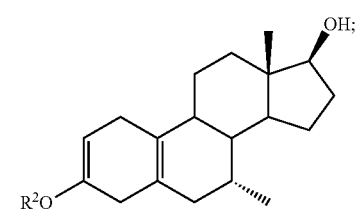
(8)

(viii) oxidizing the 17-hydroxyl group of the compound of formula (8) to produce a compound of formula (9):

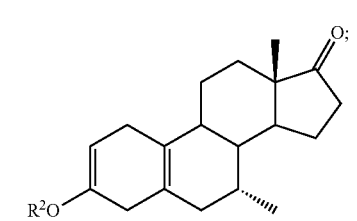
(9)

(ix) ethynylating the carbon at the 17-position of the compound of formula (9) to produce a compound of formula (10):

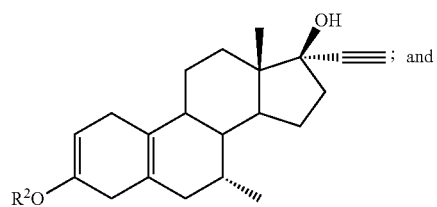
(10)

(x) removing the protecting group R² in the compound of formula (10).

2. A process according to claim 1 wherein step (i) comprises:
(a) reacting nandrolone (1) with an alkanoylating agent having the formula (RCO)₂O wherein R represents: C₁ to C₂₀ alkyl, C₆ to C₁₀ aryl, C₃ to C₈ cycloalkyl, C₇ to C₂₀ aralkyl, or C₇ to C₂₀ alkaryl, to produce a compound of formula (2);

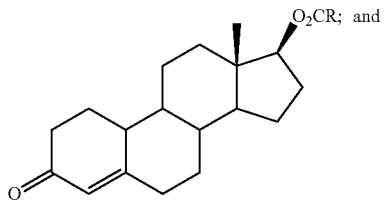
(2)

(b) reacting the compound of formula (2) with an acetylating agent having the formula R¹—CO—X, wherein R¹ represents: C₁ to C₂₀ alkyl, C₆ to C₁₀ aryl, C₃ to C₈ cycloalkyl, C₇ to C₂₀ aralkyl, or C₇ to C₂₀ alkaryl and X represents Cl, Br or I, to produce a compound of formula (3).

3. A process according to claim 1 wherein step (i) comprises reacting nandrolone (1) with a compound of formula:

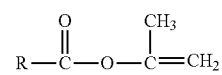

in the presence of para-toluene sulfonic acid, to form the compound of formula (3).

4. A process according to claim 1 wherein step (ii) comprises reacting the compound of formula (3) with an N-halosuccinimide, wherein halo represents Cl, Br or I.

5. A process according to claim 1 wherein step (iii) comprises reacting the compound of formula (4) with lithium halide and lithium carbonate.

6. A process according to claim 1 wherein step (iv) comprises reacting the compound of formula (5) with methylmagnesium halide in the presence of copper(II) acetate.

7. A process according to claim 1 wherein step (v) comprises reacting the compound of formula (6) with an aqueous mineral acid.

8. A process according to claim 1 wherein step (vii) comprises reacting the compound of formula (7) with calcium and liquid ammonia.

9. A process according to claim 1 wherein step (viii) comprises reacting the compound of formula (8) with an aluminium alkoxide reagent having the formula:

Al(O—Rᵃ)₃ wherein each Rᵃ is the same or different and each represents a branched C₃-C₁₀ alkyl group, a C₆ to C₁₀ aryl group, a C₃ to C₇ cycloalkyl group, a C₇ to C₂₀ aralkyl group or a C₇ to C₂₀ alkaryl group, in the presence of an aldehyde or ketone proton acceptor compound.

10. A process according to claim 9 wherein Rᵃ is a branched C₃-C₆ alkyl group.

11. A process according to claim 9 wherein the aluminium alkoxide reagent comprises Al(ⁱPrO)₃ or Al(OᵗBu)₃.

12. A process according to claim 1 wherein step (ix) comprises reacting the compound of formula (9) with ethynylmagnesium halide.

13. A process according to claim 1 wherein step (ix) comprises reacting the compound of formula (9) with sodium acetylide.

14. A process according to claim 9 wherein the proton acceptor compound comprises benzaldehyde.

15. A process according to claim 1 wherein step (x) comprises reacting the compound of formula (10) with aqueous mineral acid.

16. A process according to claim 1, wherein R, $R^1$ and $R^2$ represent methyl.

17. A process according to claim 1, wherein no chromatographic purification of the compound of formula (6) is carried out after the completion of step (v).

18. A process according to claim 1, wherein the 7α/7β epimer selectivity ratio in each of steps (iv) and (v) is greater than 4:1.

19. A process for the synthesis of tibolone (11):

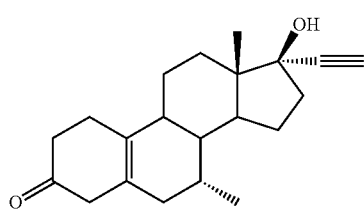

said process consisting essentially of the steps of:
(i) protecting the 17-hydroxy group and the 3-keto group of nandrolone (1)

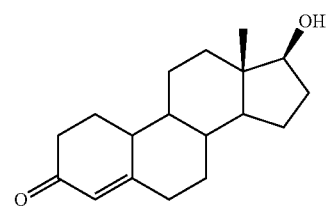

to produce a compound of formula (3):

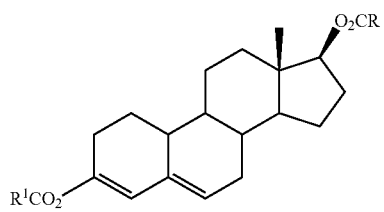

wherein R and R1 may be the same or different and each independently represents: $C_1$ to $C_{20}$ alkyl, $C_6$ to $C_{10}$ aryl, $C_3$ to $C_8$ cycloalkyl, $C_7$ to $C_{20}$ aralkyl, or $C_7$ to $C_{20}$ alkaryl;

(ii) halogenating the carbon at the 6-position of the compound of formula (3) to produce a compound of formula (4):

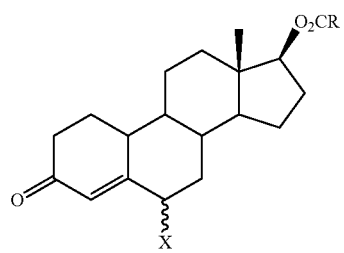

wherein X represents F, Cl, Br or I;

(iii) dehydrohalogenating the compound of formula (4) to produce a compound of formula (5):

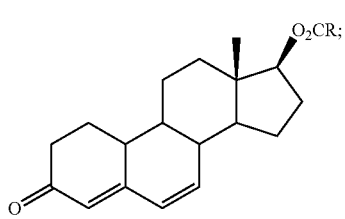

(iv) methylating the carbon atom at the 7-position of the compound of formula (5) to produce a compound of formula (5a):

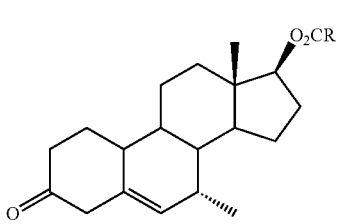

(v) isomerizing the C=C double bond of the compound of formula (5a) to produce a compound of formula (6):

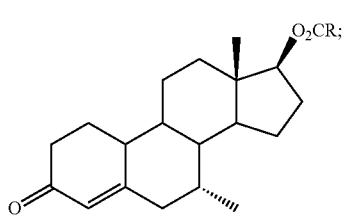

(vi) (a) dehydrogenating at a temperature of 15° C. to 30° C. the compound of formula (6) using CuBr$_2$ in the presence of an alcohol, R$^2$—OH to produce a product mixture comprising a compound of formula (7) and a compound of formula (7*):

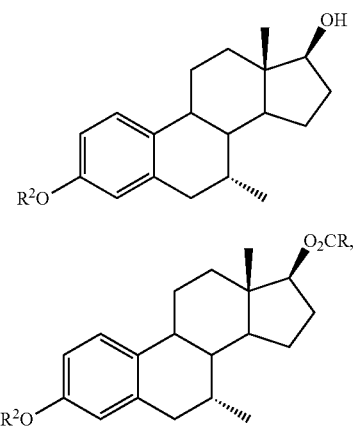

wherein R$^2$ represents C$_1$ to C$_{10}$ alkyl, C$_6$ to C$_{10}$ aryl, C$_3$ to C$_6$ cycloalkyl, C$_7$ to C$_{20}$ aralkyl or C$_7$ to C$_{20}$ alkaryl;

(vii) reducing the compound of formula (7) to produce a compound of formula (8):

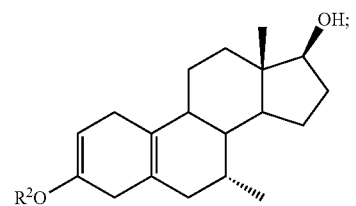

(viii) oxidizing the 17-hydroxyl group of the compound of formula (8) to produce a compound of formula (9):

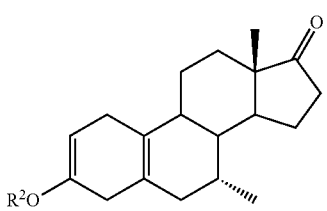

(ix) ethynylating the carbon at the 17-position of the compound of formula (9) to produce a compound of formula (10):

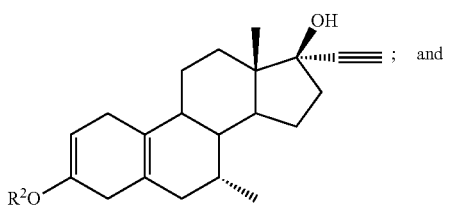

(x) removing the protecting group R$^2$ in the compound of formula (10).

* * * * *